US00PP29983P2

(12) United States Plant Patent
Kleinwee

(10) Patent No.: US PP29,983 P2
(45) Date of Patent: Dec. 11, 2018

(54) ***SUTERA* PLANT NAMED 'SUTZ0008'**

(50) Latin Name: *Sutera cordata*
Varietal Denomination: SUTZ0008

(71) Applicant: SYNGENTA PARTICIPATIONS AG, Basel (CH)

(72) Inventor: Theodorus Cornelis Maria Van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,583

(22) Filed: Jul. 3, 2017

(51) Int. Cl.
*A01H 5/02* (2018.01)

(52) U.S. Cl.
USPC ..... Plt./485
CPC ..... *A01H 5/02* (2013.01)

(58) Field of Classification Search
USPC ..... Plt./485
CPC ..... A01H 5/02
See application file for complete search history.

(56) References Cited

PUBLICATIONS

PLUTO UPOVROM Plant Variety Database Citation for 'Sutz0008'; Oct. 28, 2016; 1 page.*

* cited by examiner

*Primary Examiner* — Kent L Bell
(74) *Attorney, Agent, or Firm* — Dale Skalla

(57) ABSTRACT

A new *Sutera* plant named 'SUTZ0008' particularly distinguished by its compact to semi trailing plant habit, good branching, lavender flower color and medium to dark green, deltoid shaped leaves.

1 Drawing Sheet

Figure 1:
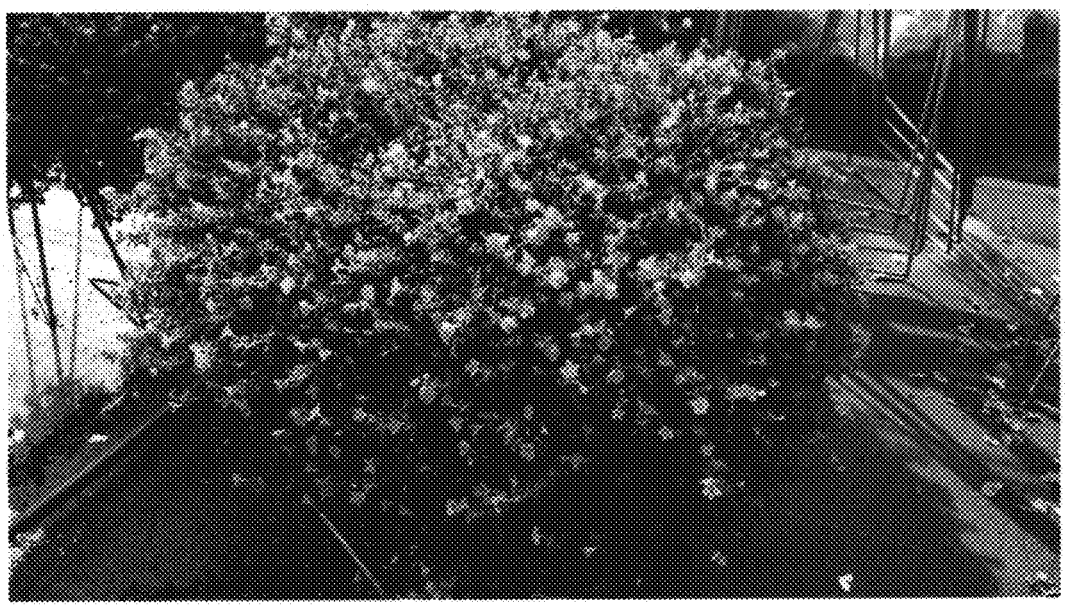
Figure 2:
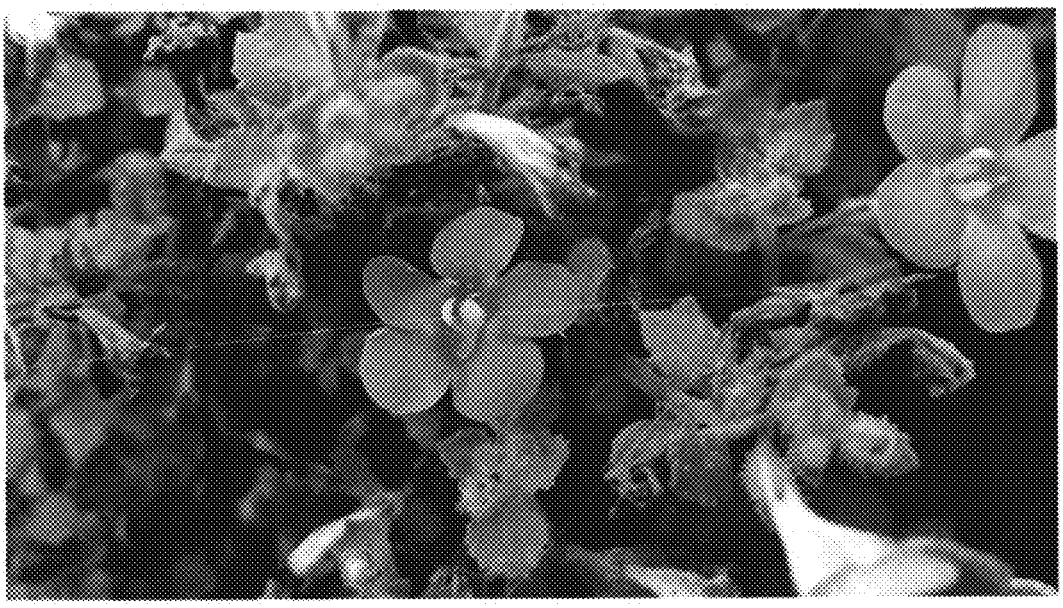

Latin name of the genus and species of the plant claimed: *Sutera cordata.*

Varietal denomination: 'SUTZ0008'.

BACKGROUND OF THE NEW PLANT

The present invention comprises a new *Sutera*, botanically known as *Sutera cordata*, and hereinafter referred to by the variety name 'SUTZ0008'.

'SUTZ0008' is a product of a planned breeding program. The new cultivar has large sized lavender colored flowers, medium to dark green foliage, compact to semi trailing plant habit with good branching. The new cultivar is very floriferousness.

'SUTZ0008' originated from a cross conducted during the summer of 2012 between a line designated 'M0049.1' as the female parent and a line designated 'BA12-0071-1' as the male parent. The resultant seed was sown in a controlled breeding environment in the fall of 2012 in Enkhuizen, The Netherlands. In January 2013, 'SUTZ0008' was selected as one flowering plant within the progeny of the stated cross in summer 2012 in Enkhuizen, The Netherlands.

The first act of asexual reproduction of 'SUTZ0008' was accomplished when vegetative cuttings were propagated from the initial selection in February 2013 in a controlled environment in Enkhuizen, The Netherlands.

BRIEF SUMMARY OF INVENTION

Horticultural examination of plants grown from cuttings of the plant initiated in March 2013, and continuing thereafter, has demonstrated that the combination of characteristics as herein disclosed for 'SUTZ0008' are firmly fixed and are retained through successive generations of asexual reproduction.

'SUTZ0008' has not been observed under all possible environmental conditions. The phenotype may vary significantly with variations in environment such as temperature, light intensity and day length.

A Plant Breeder's Right for this cultivar was applied for in the European Union on Oct. 28, 2016, No. 2016/2632. 'SUTZ0008' has not been made publicly available prior to the effective filing date of this application, notwithstanding any disclosure that may have been made less than one year prior to the effective filing date of this application by the inventor or another who obtained 'SUTZ0008' directly from the inventor.

The following traits have been repeatedly observed and are determined to be basic characteristics of the new variety. The combination of these characteristics distinguishes this *Sutera* as a new and distinct variety.

BRIEF SUMMARY OF THE INVENTION

The following observations, measurements, and comparisons describe plants grown indoors and outdoors in Andijk and Enkhuizen, The Netherlands and Gilroy, Calif., United States. The following traits have been repeatedly observed and are determined to be basic characteristics of the new variety. The combination of these characteristics distinguishes this *Sutera* as an improved and distinct variety:

1. 'SUTZ0008' is a lavender flowering *Sutera* with rather large flowers
2. Medium-dark green deltoid leaves.
3. Compact to semi trailing plant with good branching.

COMPARISON WITH COMMERCIAL VARIETIES

'SUTZ0008' is more floriferous than the female parent, 'M0049.1' and much more floriferous than the male parent, 'BA12-0071-1'.

'SUTZ0008' differs from the commercial *Sutera* cultivar 'Cal Julav' in that 'SUTZ0008' is a new color, better branched, more compact and by far more floriferous.

'SUTZ0008' differs from the commercial *Sutera* cultivar 'Gulliver Dynamic White', protected as U.S. Plant Pat. No. 21,098, in that 'SUTZ0008' is a bit more compact, a bit better branched and more floriferous.

BRIEF DESCRIPTION OF THE PHOTOGRAPHS

The accompanying photographic drawing shows typical flower and foliage characteristics of 'SUTZ0008' with colors being as true as possible with an illustration of this type. The first and second photographic drawing shows a flowering potted plant of the new variety and a close-up of the flowers.

DETAILED BOTANICAL DESCRIPTION

All mentioned photographs were taken in October 2015 of a plant in 12 cm pot grown in a greenhouse in Enkhuizen, The Netherlands. The plants were 17 weeks old. Color references are made to The Royal Horticultural Society Colour Chart (R.H.S.) 2001.

TABLE 1

| | 'SUTZ0008' | 'CAY JULAV' |
|---|---|---|
| Flower diameter: | Bigger than 'CAY JULAV' | Smaller than 'SUTZ0008' |
| Bleaching in high light: | Hardly bleaching | Does bleach in high light |
| Habit: | Compact to semi trailing | Semi trailing to trailing |
| Flower color: | Deeper lavender color | Lavender color |

VARIETAL DENOMINATION

Plant:

*Growth and habit*.—Dense, compact to semi trailing.
*Height*.—6-10 cm (above soil).
*Spread* (*including flowers*).—30-38 cm.
*Number of branches*.—50.
*Time to produce a finished flowering plant*.—11-12 weeks for 12 cm pot.
*Outdoor plant performance*.—Used for hanging baskets, mixed container plantings, is very floriferous.
*Time to initiate and develop roots*.—21 days at 19-22° C.
*Root description*.—Fine, fibrous and freely branching.

Stem:

*Characteristics*.—Cross section round, high degree of self-branching.
*Stem length*.—6-28 cm.
*Diameter*.—2-3 mm.
*Internode length*.—0.5-3.5 cm.
*Color*.—RHS 138B.
*Texture*.—Hirsute.

Foliage:

*Arrangement*.—Opposite, decussate.
*Leaf shape*.—Deltoid.
*Apex*.—Acute.
*Base*.—Attenuate.
*Margin*.—Serrate.
*Leaf length*.—Up to 2.0 cm.
*Leaf width*.—Up to 2.0 cm.
*Immature leaf, color upper surface*.—RHS 137C.
*Immature leaf, color lower surface*.—RHS 137D.
*Mature color upper surface*.—RHS 137A.
*Mature color lower surface*.—RHS 137B.
*Venation type*.—Palmate.
*Venation color*.—RHS 141C.
*Texture*.—Light pubescent on both sides; more dense pubescent on veins of lower side.

Petiole:

*Length*.—0.6 cm.
*Petiole width*.—2 mm.
*Petiole color*.—RHS 141C.
*Texture*.—Pubescent.

Inflorescence:

*Blooming habit*.—When temperatures don't exceed 25° C. it will bloom with many flowers through the growing season from spring to fall.
*Type of inflorescence*.—Solitary, flowers emerge from the leaf axils of the upper stem nodes, usually 2 flowers per node.
*Quantity of flowers per stem*.—Usually 2 flowers.
*Fragrance*.—None.

Pedicel:

*Color*.—RHS 143A.
*Length*.—0.3-0.5.
*Diameter*.—0.1 cm.
*Texture*.—Densily pubescent.

Flower:

*Corolla type and shape*.—Single-type, nearly round, lower part funnel-shaped formed by 5, mainly fused petals. Upper part is salver-shaped formed by the partly free petal lobes.
*Corolla diameter*.—Up to 1.5 cm.
*Flower length*.—About 1.2 cm.
*Funnel diameter*.—0.4 cm.
*Color upper surface*.—RHS N87B.
*Color lower surface*.—RHS N87C.
*Color of throat*.—RHS 23A.
*Color of funnel outer side*.—RHS 21A.

Petal (lobes):

*Apex*.—Rounded.
*Base*.—Fused.
*Margin*.—Entire.
*Texture*.—Upper side is smooth glabrous, bit puberulous in the throat. Under side glabrous to very short pubescence, increasing on the corolla tube.
*Length of lobes*, (*from the corolla opening*).—0.6 cm.
*Width of lobes*.—1.0 cm.

Flower bud:

*Shape*.—Cone-shaped.
*Diameter*.—0.2-0.6 cm.
*Length*.—0.2-1.0 cm.
*Color* (*at tight bud*).—RHS 157D at base, RHS 14C middle, RHS N87A at top.

Calyx:

*Shape*.—5 sepals in a whorl around the flower base.
*Sepal shape*.—Lanceolate, fused at the base.

*Sepal color*.—RHS 143A.
*Length*.—0.5 cm.
*Width*.—About 1 mm.
*Apex*.—Acute.
*Base*.—Fused.
*Texture*.—Covered with dense hair.

Reproductive organs:

Stamens:

*Quantity*.—4.
*Filament, color*.—White, RHS N155B.
*Length*.—0.8 cm.
*Diameter*.—0.1 cm.
*Anther color*.—Yellow, RHS 14A.
*Pollen amount*.—Abundant.
*Pollen color*.—Yellow, RHS 14A.

Pistil:

*Quantity per flower*.—One.
*Length*.—0.9 cm.
*Stigma color*.—Light green, Darker than RHS 157A.
*Style color*.—Greenish white, RHS 157A.

Fruit and seed set: Has not been observed.

Disease and insect resistance: Resistance and susceptibility typical for the species, no special observations made.

What is claimed is:

1. A new and distinct cultivar of *Sutera* plant named 'SUTZ0008' substantially as illustrated and described herein.

* * * * *